United States Patent
Xie et al.

(10) Patent No.: US 7,662,406 B1
(45) Date of Patent: Feb. 16, 2010

(54) CHEWABLE SOFTGEL CAPSULES

(75) Inventors: Xueju Xie, Richmond (CA); Yu-Lung Ko, Richmond (CA); Chien-Kuang Ko, Richmond (CA); Jason Jiang-Chung Ko, Richmond (CA)

(73) Assignee: Viva Pharmaceutical Inc., Richmond, British Columbia (CA)

( * ) Notice: Subject to any disclaimer, the term of this patent is extended or adjusted under 35 U.S.C. 154(b) by 0 days.

(21) Appl. No.: 12/543,435

(22) Filed: Aug. 18, 2009

Related U.S. Application Data

(63) Continuation of application No. 12/537,092, filed on Aug. 6, 2009.

(51) Int. Cl.
*A61K 9/48* (2006.01)
*A61K 9/64* (2006.01)
*A61K 9/66* (2006.01)

(52) U.S. Cl. .................. 424/451; 424/455; 424/456

(58) Field of Classification Search .................. 424/451, 424/455, 456
See application file for complete search history.

(56) References Cited

U.S. PATENT DOCUMENTS

| | | | |
|---|---|---|---|
| 4,609,403 A | 9/1986 | Wittwer et al. | |
| 5,817,323 A | 10/1998 | Hutchinson et al. | |
| 6,258,380 B1 | 7/2001 | Overholt | |
| 2003/0232076 A1 | 12/2003 | Makino et al. | |

FOREIGN PATENT DOCUMENTS

WO    WO 2008/106787    9/2008

*Primary Examiner*—Robert A Wax
*Assistant Examiner*—Aradhana Sasan
(74) *Attorney, Agent, or Firm*—Fasken Martineau DuMoulin LLP

(57) ABSTRACT

A chewable softgel capsule configured for encasing orally ingestible articles. The chewable soft capsule is provided with an outer shell composition which comprises at least one gelatin in a range of 20% to 60% of the total weight of the shell composition, at least one plasticizer in an amount selected to render flexible the outer shell composition, an anti-tacking agent in an amount selected to render the outer shell composition non-sticky, and water. In one embodiment the chewable soft capsule further comprises at least one starch in a range of 0.1% to 35% of the total weight of the shell composition. The chewable softgel capsule is suitable for encasing therein medicines, pharmaceutical compositions, nutraceuticals, vitamins, nutritional supplements, and the like.

12 Claims, No Drawings

CHEWABLE SOFTGEL CAPSULES

CROSS-REFERENCE TO RELATED APPLICATIONS

This application is a continuation of application Ser. No. 12/537,092 filed Aug. 6, 2009, which is a continuation-in-part of application Ser. No. 12/200,850 filed Aug. 28, 2008 currently pending.

FIELD OF THE INVENTION

The present invention relates generally to soft gelatin capsules and in particular, to soft gelatin capsules having a chewable consistency.

BACKGROUND OF THE INVENTION

Common routes for the administration of pharmacologically active agents, nutraceuticals, and vitamins are exemplified by a variety of oral dosage forms such as tablets, pills, and capsules. Additionally, a wide range of foodstuffs and oral hygiene products, such as breath fresheners are also orally dispensed. Such dosage forms are generally convenient, stable in storage and transport, and familiar to the user. However, they are not without problems, and these problems are often significant. It is extremely difficult for most people to swallow any of these oral dosage forms without supplemental water. It is frequently inconvenient or messy to have to take supplementary water with oral medicaments. Such difficulties are compounded for those with swallowing difficulties such as, for example, children and the elderly. Certain medical conditions, such as Parkinsons' disease and other neurological states, make it difficult to swallow oral dosage forms, even with supplemental water.

Children and the elderly often experience difficulty in swallowing and ingesting medicines in solid forms such as tablets, pills, and capsules. Pharmaceuticals in forms which permit easy ingestion and whose active components are rapidly released in the oral cavity are desirable in the event of a medical emergency such as an attack of angina pectoris.

Recently, with diversification of personal preferences in food and textures of food within the mouth, the texture of oral dosage forms of pharmaceuticals is an additional complication in oral medicaments.

In conventional soft gelatin capsules, ingredients are encapsulated in a gelatin shell for consumption. Generally, the shell of a soft gelatin capsule comprises gelatin and a plasticizer to control the softness and flexibility of the shell. The shell further includes water and optionally other additives such as flavorants. The shells are typically dried until the water content is decreased to a certain level so as to prevent the capsule from being deformed or becoming undesirably sticky.

Conventional soft gelatin capsules commonly available are often hard and tough because they are designed to dissolve after reaching the intestines so as to release their contents therein. Such capsules are not easily broken by teeth and are not suitable for chewing. In addition, twisting the capsule with the fingers to open the capsule is often a difficult practice, and generally opening the capsule requires a tool such as scissors. One measure to soften a soft gelatin capsule is to increase the plasticizer content and increase the capsule flexibility. However, this often makes a soft gelatin capsule more likely to stick to another soft gelatin capsule or to a container, thereby causing deterioration in storage stability. Increasing plasticizer content is further problematic in high-temperature, high-humidity regions. Soft gelatin capsules with acceptable dosing, stability, and storage and handling characteristics are typical when a relatively high gelatin content and a relatively low plasticizer and end water content is found in the capsules. However, the chewability, texture and mouth feel, and client acceptance of the capsules are found when a lower gelatin content and higher plasticizer and end water contents is used.

Typically, chewable soft gelatin capsules, or chewable softgels, are designed such that the user chews upon the capsule to release the fill into the mouth instead of swallowing the capsule with the fill still encapsulated within the shell. Furthermore, these chewable softgels are intended to be completely or nearly completely dissolved by chewing. Such capsules are distinguished by particular fabrication problems, such as excessive stickiness during encapsulation and sticking of the end product to other capsules during post-encapsulation handling. Further, chewable softgels with high end water content typically have poor storage performance, sticking to one another in packaging and often melting or leaking during storage. In addition to the effects of water content, chewability of capsules can be affected by the bloom strength and the melting points of the gelatin used. In general, gelatins of lower bloom strength and lower melting point have preferable organoleptic qualities.

U.S. Pat. No. 4,935,243 to Borkan, et al. discloses a chewable gelatin capsule composition that comprises less than about 30%, and preferably comprises about 20-26% water, and is directed to the use of a hydrogenated starch hydrolysate, which allowed a lower than expected end water content. U.S. Pat. No. 4,532,126 to Ebert, et al. discloses examples of soft gelatin capsules formed at as high as 37% water content, but specifies that these capsules were then subsequently dried to some undisclosed final end water content, in order to obtain desired chewing characteristics.

U.S. Pat. No. 3,851,051 to Miskel et al. discloses numerous embodiments of a soft gelatin capsule that has an initial capsule shell water content of between 28.3 and 36.6%, but further discloses that the capsules are then dried to be in equilibrium with the internal gel-lattice composition, which has a water content of 15-20%. In U.S. Pat. No. 6,258,380 to Overholt, capsules are fabricated from a wet mass that is initially as much as 30% water by weight, but is then subsequently dried to 6%-8% water.

U.S. patent application Ser. No. 10/456,450 to Makino; accomplished a high degree of hydration using fish gelatin having a low sol-gel transition temperature, that is, a relatively low melting point. However, such formulations can be problematic when stored at high temperatures or high humidity. For example, it is very difficult to formulate a fish gelatin capsule that will be stable at a storage temperature above 35° C. Capsules made with such low melting point gelatins tend to become sticky during storage, and may even burst or melt, releasing their contents. On the other hand, it is known that mammalian gelatins, some of which have melting temperatures above 60° C., tend to be much more stable at higher storage temperatures, but too often have poorer organoleptic qualities.

There is a need for chewable softgel compositions having commercially acceptable properties at the time the capsules are packaged and made available for sale. Additionally, these chewable capsules should exhibit stability under reasonably expected storage times and conditions. Further, these capsules need to exhibit a soft, pleasant chewing texture and low stickiness.

BRIEF SUMMARY OF THE INVENTION

The exemplary embodiments of the present invention relate to chewable softgel capsules suitable for encasing orally ingested articles, and to processes for producing such chewable softgel capsules.

An exemplary embodiment of the present invention relates to a chewable soft capsule having an outer shell composition comprising at least one gelatin in an amount selected from the range of 20% to 60% of the total weight of the shell composition, at least one plasticizer in an amount selected to render flexible said outer shell composition, an anti-tacking and softening agent in an amount selected to render said outer shell composition non-sticky and soft, and water.

According to one aspect the outer shell composition of the chewable softgel capsule may optionally comprise at least one starch in an amount selected from the range of 0.1% to 35% of the total weight of the shell composition.

According to one aspect, the gelatin is selected from the group consisting of an animal-derived gelatin, a chemically modified gelatin, a physically modified gelatin, and combinations thereof.

According to another aspect, the anti-tacking and softening agent is selected from the group consisting of lecithin, polysorbate, biologically derived waxes, chemically derived waxes, fats, oils and combinations thereof.

According to another aspect, the oil is selected from the group consisting of palm oil, coconut oil, vegetable oil, middle chain triglycerins and mixtures thereof.

According to yet another aspect, the plasticizer is selected from the group consisting of glycerin, mannitol, polyethylene glycol, sorbitol, sorbitol special, propylene glycol, maltitol, sucrose, corn syrup, fructose, cellulose, disodium sulfosucciante, triethyl citrate, tributyl citrate, 1-2-propylenglycol, natural gum, isomerized sugar, xylitol, polyglycerol, glucose syrups, glucose, sugar alcohol, and combinations thereof.

According to a further aspect, the starch is selected from the group consisting of native starches, modified starches, polysaccharides, and combinations thereof.

According to another further aspect, the outer shell composition of the chewable softgel capsule may optionally comprise at least one of a flavorant, a colorant, a preservative, and optionally, combinations thereof.

Another exemplary embodiment of the present invention is relates to a process for making the chewable softgel capsules. The process generally comprises the steps of selecting a suitable amount of gelatin, selecting a suitable amount of plasticizer, selecting a suitable amount of starch, selecting a suitable amount of anti-tacking and softening agent, placing predetermined amounts of said selections into a cooking tank and adding a predetermined amount of water, mixing selections for at least 2 hours at 80-90° C., reducing the temperature of the mixture in the cooking tank to 55-65° C. until all air bubbles are removed from the mixture, transferring the mixture from the cooking tank to a machine configured for producing chewable softgel capsules from the mixture, and then producing chewable softgel capsules from the mixture with the machine.

DETAILED DESCRIPTION OF THE INVENTION

Some exemplary embodiments of the present invention relate to a chewable softgel capsule exhibiting extended storage stability, a soft chewing texture and low stickiness. Further, the chewable softgel capsule exhibits excellent manufacturing properties and can be produced using conventional encapsulation machinery known in the art.

Some exemplary embodiments of the present invention relate to a chewable softgel capsule encasing an orally ingestible article, where the capsule having an outer shell composition comprising: at least one gelatin; at least one plasticizer in an amount sufficient to render the outer shell flexible; at least one starch; an anti-tacking and softening agent sufficient to render said outer shell non-sticky during manufacturing processes; and purified water. The capsule outer shell may optionally further include at least one of flavorants, colorants, and preservatives.

Surprisingly, it has been found that the chewable softgel capsule of the present invention may be produced by mixing an anti-tacking and softening agent, for example lecithin and or beewax, with gelatin, plasticizer, and starch. The softgel capsules produced from this mixture are non-sticky at a high moisture content of about 20% thereby facilitating their processing and production. In addition, the softgel capsule remains very soft and pliable, even at low moisture contents of about 3%. Moreover, the softgel capsules remain non-sticky and soft during extended storage, for example, in conditions of 40° C., 75% RH.

The composition of the present chewable softgel capsule utilizes the starch component, when mixed with the gelatin and plasticizer, to form a matrix in which the anti-tacking and softening agent is trapped so as to produce the chewable softgel capsule of the present invention. The starch does not act as a moisture retention agent as understood in the prior art. This anti-tacking and softening agent when used in the formulations disclosed by the present invention enables the production of a softgel capsule which: is non-sticky under storage conditions of high temperature and humidity for example, 40° C., 75% RH; and is non-sticky and soft at both low e.g. 3%, and high e.g. 24%, capsule moisture content.

Some exemplary embodiments of the present invention related to a softgel capsule encasing an orally ingestible article, the capsule having an outer shell composition comprising at least (a) at least one gelatin, preferably between about 20 to 60% weight, more preferably between about 20 to 50% weight, even more preferably between about 30 to 47% weight; (b) at least one plasticizer in an amount sufficient to render said outer shell flexible, preferably between about 25 to 45% weight; (c) an anti-tacking and softening agent sufficient to render the outer shell non-sticky and soft, preferably 0.2 to 15% weight, more preferably between about 0.4 to 10% weight, even more preferably 0.6 to 5% weight; and (d) purified water, preferably between about 3 to 25% weight, more preferably between about 3 to 20% weight. The capsule outer shell further includes (e) at least one starch, preferably between about 0.1 to 35% weight, more preferably between about 2 to 25% weight, even more preferably between about 10 to 20% weight. The capsule outer shell may optionally further include (f) at least one of flavorants, colorants, and preservatives.

Some exemplary embodiments of the present invention relate to at least one plasticizer selected from the group consisting of glycerin, mannitol, polyethylene glycol, sorbitol, sorbitol special, propylene glycol, maltitol, sucrose, corn syrup, fructose, cellulose, disodium sulfosucciante, triethyl citrate, tributyl citrate, 1-2-propylenglycol, natural gum, isomerized sugar, xylitol, polyglycerol, glucose syrups, glucose, sugar alcohol, and combinations thereof.

Some exemplary embodiments of the present invention relate to at least one gelatin selected from the group consisting of animal-derived gelatin, chemically modified gelatin, physically modified gelatin, and combinations thereof. A particularly suitable animal-derived gelatin may be derived from pigskin or alternatively bovine bone.

Some exemplary embodiments of the present invention relate to incorporation into the present chewable soft gelatin capsule composition of at least one starch exemplified by native starches and modified starches. Suitable native starches are exemplified by potato starches, corn starches, wheat starches, oat starch, barley starch, rice starches, sorghum starches, and tapioca starches. Modified starches are native starches that have been partially degraded by physical treatments or alternatively, by chemical treatments, and are commonly referred to as physically modified starches and chemically modified starches.

Suitable physical treatments are exemplified by pre-gelatinization and by heat-moisture treatments. Suitable physically modified starches are exemplified by physically modified potato starches, physically modified corn starches, physically modified wheat starches, physically modified oat starch, physically modified barley starch, physically modified rice starches, physically modified sorghum starches, and physically modified tapioca starches.

Suitable chemical treatments are exemplified by alkali washes, washes with inorganic acids, enzymatic hydrolysis, bleaching, oxidation, esterification, etherification, cross-linking, ionization, and combinations of these modifications such as acetylation and oxidation. Suitable chemically modified starches are exemplified by esterified starch, starch phosphate, etherified starches, cross-linked starches, cationized starches, enzymatically digested starches, oxidized starches, and combinations thereof.

Some exemplary embodiments of the present invention relate to a softgel capsule where the anti-tacking and softening agent is preferably between about 0.2 to 15% weight, more preferably between about 0.4 to 10% weight, and even more preferably between about 0.6 to 5% weight.

Some exemplary embodiments of the present invention relate to an anti-tacking and softening agent selected from the group consisting of: lecithin, polysorbate such as Tween 60 or 80, biologically derived waxes, chemically derived waxes, fats, oils or combinations thereof.

Some exemplary embodiments of the present invention relate to an anti-tacking and softening agent where it is preferably one of beeswax, lecithin, palm oil and coconut oil.

The following Examples illustrate practical formulations of chewable softgel capsules of the present invention. It is to be understood these examples should not be considered as limitations, the experimental data is only for illustration.

Example 1

Softgel Capsules, Formulation A, without Anti-Tacking and Softening Agent

Conventional softgel capsules known in the art were prepared according to the following method. A mixture of gelatin, glycerin, potato starch, stevia extract, orange flavor and water, in the proportions as indicated in Table 1 below, up to a weight of 200 kg were placed in a cooking tank with 800 L of capacity. The cooking tank was heated to 80-90° C. and the temperature was maintained for a period of 1-3 hours. The temperature of the cooking tank was then reduced to 55° C. until air bubbles were about completely removed. Chewable soft capsules of 20-oval size were produced using conventional soft capsule machinery and were filled with seal oil.

TABLE 1

| Item Name | % weight |
|---|---|
| Gelatin 170-180 Bloom Pigskin | 33.58 |
| Glycerin 99.5% | 28.79 |
| Potato Starch | 11.5 |
| Stevia extract | 0.0144 |
| Orange Flavor | 0.191 |
| Purified Water | 26.0 |

Exemplary embodiments of the softgel capsules of the present invention disclosed above are detailed in Examples 2-4 below.

Example 2

Improved Softgel Capsule, Formulation B

A mixture of gelatin, glycerin, potato starch, lecithin, stevia extract, orange flavor and water, in the proportions as indicated in Table 2 below, up to a weight of 200 kg were placed in a cooking tank with 800 L of capacity. The cooking tank was heated to 80-90° C. and the temperature was maintained for a period of 1-3 hours. The temperature of the cooking tank was then reduced to 55° C. until air bubbles were about completely removed. Chewable soft capsules of 20-oval size were produced using conventional soft capsule machinery and were filled with seal oil.

TABLE 2

| Item Name | % weight |
|---|---|
| Gelatin 170-180 Bloom Pigskin | 33.58 |
| Glycerin 99.5% | 28.79 |
| Potato Starch | 11.5 |
| Lecithin | 0.96 |
| Stevia extract | 0.0144 |
| Orange Flavor | 0.191 |
| Purified Water | 24.96 |

Example 3

Improved Softgel Capsule, Formulation C

A mixture of gelatin, glycerin, potato starch, palm oil, aspartame, acesulfame-K, orange flavor and water, in the proportions as indicated in Table 3 below, up to a weight of 200 kg were placed in a cooking tank with 800 L of capacity. The cooking tank was heated to 80-90° C. and the temperature was maintained for a period of 1-3 hours. The temperature of the cooking tank was then reduced to 55° C. until air bubbles were about completely removed. Chewable soft capsules of 20-oval size were produced using conventional soft capsule machinery and were filled with multi-vitamins paste.

TABLE 3

| Item Name | % weight |
|---|---|
| Gelatin 170-180 Bloom Pigskin | 34 |
| Glycerin 99.5% | 28 |
| Potato Starch | 10.0 |
| Palm Oil | 1.5 |
| Aspartame | 0.190 |
| Acesulfame-K | 0.199 |
| Orange Flavor | 0.191 |
| Purified Water | 25.92 |

Example 4

Improved Softgel Capsule, Formulation D

A mixture of gelatin, glycerin, potato starch, beeswax, stevia extract, mango flavor and water, in the proportions as indicated in Table 2 below, up to a weight of 200 kg were placed in a cooking tank with 800 L of capacity. The cooking tank was heated to 80-90° C. and the temperature was maintained for a period of 1-3 hours. The temperature of the cooking tank was then reduced to 55° C. until air bubbles were about completely removed. Chewable soft capsules of 20-oval size were produced using conventional soft capsule machinery and were filled with seal oil.

TABLE 4

| Item Name | % |
| --- | --- |
| Gelatin 170-180 Bloom Pigskin | 33 |
| Glycerin 99.5% | 26 |
| Potato Starch | 12 |
| beewax | 1.0 |
| *Stevia* extract | 0.0144 |
| Mango Flavor | 0.191 |
| Purified Water | 27.79 |

Two samples of the resulting capsules for each formulation were taken at a plurality of time points. These time points included: immediately after production (i.e. encapsulation); following 20-minutes of drying in a tumbler; after drying overnight in a room at 21° C., 23% room humidity (RH); and after drying in a room for three days at 21° C., 23% RH. The capsule samples for each time point and each formulation were packaged in glass bottles and sealed. Each sample comprised at least 86 soft capsules. A first set of samples was tested after being stored for a period of 2 weeks at 40° C. and 75% RH. A second set of samples was tested after being stored for a period of 12 months at 25° C. and 35% RH.

The results of the comparison of samples for each of the formulations taken at different time points and then stored under different conditions are shown in Table 5. The samples of the capsules at each time point had variable degrees of capsule shell moisture ranging from 3%-24%. Despite the variable in shell moisture content, each of the formulations (B, C, and D) of the present invention exhibited no stickiness and softness under either set of the storage conditions tested. However, the capsule from formulation A containing no anti-tacking and softening agent showed stickiness for each sample time-point tested under both sets of storage conditions. In addition, the capsule formulation A produced capsules which were significantly harder than the formulations of the present invention, especially when the shell moisture is lower than 11%. In Table 5, N represents no sticky, Y represents sticky, S represents soft, and H represents hard.

TABLE 5

| | | Formulation B | | | Formulation C | | | Formulation D | | | Formulation A containing no anti-tacking and soften agent | | |
| --- | --- | --- | --- | --- | --- | --- | --- | --- | --- | --- | --- | --- | --- |
| | Timepoints | % Shell Moisture | 2 weeks | 12 months | % Shell Moisture | 2 weeks | 12 months | % Shell Moisture | 2 weeks | 12 months | % Shell Moisture | 2 weeks | 12 months |
| Sample 1 | Immediately following production | 22% | NS | NS | 23% | NS | NS | 24% | NS | NS | 22% | YS | YS |
| Sample 2 | After drying for 30 mins in a tumbler | 11% | NS | NS | 11% | NS | NS | 12% | NS | NS | 11% | YH | YH |
| Sample 3 | After drying overnight 21° C., 23% RH | 6% | NS | NS | 7% | NS | NS | 7% | NS | NS | 6% | YH | YH |
| Sample 4 | After drying for 3 days 21° C., 23% RH | 3% | NS | NS | 3% | NS | NS | 4% | NS | NS | 3% | YH | YH |

Example 5

Comparison of Improved Softgel Capsules of Formulation B-D with Softgel Capsules of Formulation A Each of the chewable soft capsules described in examples 1-4 were prepared and produced using the same methods.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the inven-

The invention claimed is:

1. A chewable softgel capsule for encasing therein orally ingestible articles, the chewable soft capsule having an outer shell composition with a moisture content of about 3% to about 12% of the total weight of the shell composition, said outer shell composition comprising:
   at least one medium bloom gelatin incorporated thereinto, said at least one medium bloom gelatin selected from the group consisting of an animal-derived gelatin, a chemically modified gelatin, a physically modified gelatin, and combinations thereof, the amount of said gelatin selected from the range of about 30% to about 47% of the total weight of the shell composition;
   at least one plasticizer incorporated thereinto, said at least one plasticizer in an amount sufficient to render said outer shell composition flexible, said plasticizer selected from a group consisting of glycerin, mannitol, polyethylene glycol, sorbitol, sorbitol special, propylene glycol, maltitol, sucrose, corn syrup, fructose, cellulose, disodium sulfosuccinate, triethyl citrate, tributyl citrate, 1-2-propylene glycol, natural gum, isomerized sugar, xylitol, polyglycerol, glucose syrups, glucose, sugar alcohol, and combinations thereof, the amount of said plasticizer selected from the range of about 25% to about 45% of the total weight of the shell composition;
   at least one starch incorporated thereinto, said at least one starch selected from a group consisting of native starches, physically modified starches, chemically modified starches selected from a group consisting of starch succinate, starch phosphate, etherified starches, esterified starches, cross-linked starches, cationized starches, enzymatically digested starches, oxidized starches, and combinations thereof, the amount of said starch selected from the range of about 10% to about 20% of the total weight of the shell composition; and
   an anti-tacking and softening agent incorporated thereinto in an amount sufficient to render said outer shell composition non-sticky and soft therethrough, said anti-tacking and softening agent selected from a group consisting of lecithin, polysorbate, biologically derived waxes, chemically derived waxes, fats, oils, and combinations thereof, the amount of said anti-tacking and softening agent selected from the range of about 0.2% to about 3% of the total weight of the shell composition.

2. A chewable softgel capsule according to claim 1, wherein said starch is a native starch selected from a group consisting of native potato starches, native corn starches, native wheat starches, native oat starches, native barley starches, native rice starches, native sorghum starches, and tapioca starches.

3. A chewable softgel capsule according to claim 1, wherein said chemically modified starch selected from a group consisting of chemically modified potato starches, chemically modified corn starches, chemically modified wheat starches, chemically modified rice starches, chemically modified sorghum starches, chemically modified oat starches, chemically modified barley starches, and chemically modified tapioca starches.

4. A chewable softgel capsule according to claim 1, wherein said starch is a physically modified starch selected from a group consisting of pre-gelatinized starches and heat-moisture treated starches.

5. A chewable softgel capsule according to claim 4, wherein the physically modified starch selected from a group consisting of physically modified potato starches, physically modified corn starches, physically modified wheat starches, physically modified barley starches, physically modified oat starches, physically modified rice starches, physically modified sorghum starches, and physically modified tapioca starches.

6. A chewable softgel capsule according to claim 1, further comprising one of flavorants, colorants, and preservatives.

7. A process for making the chewable softgel capsules of claim 1, the process comprising the steps of:
   (a) selecting a medium bloom gelatin;
   (b) selecting a plasticizer;
   (c) selecting a starch;
   (d) selecting an anti-tacking and softening agent;
   (e) placing predetermined amounts of said selections for a medium bloom gelatin, a plasticizer, a starch and an anti-tacking and softening agent into a cooking tank and intermixing thereinto a predetermined amount of water thereby preparing a mixture therefrom;
   (f) cooking said mixture for at least 1 hour at a temperature selected from the range of about 65° C. to about 90° C.;
   (g) applying a vacuum to the mixture to remove air bubbles therefrom;
   (h) reducing the temperature of said cooking tank to a temperature selected from the range of about 55° C. to about 65° C. until all air bubbles are removed therefrom said mixture;
   (i) transferring the mixture to a machine configured for producing therein a plurality of chewable softgel capsules from said contents;
   (j) producing a plurality of chewable softgel capsules with said machine; and
   (k) drying said chewable softgel capsules to a final moisture content from about 3% to about 12%.

8. A process according to claim 7, wherein the starch is a native starch selected from a group consisting of native potato starches, native corn starches, native wheat starches, native oat starches, native barley starches, native rice starches, native sorghum starches, and tapioca starches.

9. A process according to claim 7, wherein the starch is a chemically modified starch selected from a group consisting of esterified starches, etherified starches, cross-linked starches, cationized starches, enzymatically digested starches, and oxidized starches.

10. A process according to claim 9, wherein the chemically modified starch is selected from a group consisting of chemically modified potato starches, chemically modified corn starches, chemically modified wheat starches, chemically modified oat starches, chemically modified barley starches, chemically modified rice starches, chemically modified sorghum starches, and chemically modified tapioca starches.

11. A process according to claim 7, wherein the starch is a physically modified starch selected from a group consisting of pre-gelatinized starches and heat-moisture treated starches.

12. A process according to claim 11, wherein the physically modified starch is selected from a group consisting of physically modified potato starches, physically modified corn starches, physically modified wheat starches, physically modified oat starches, physically modified barley starches, physically modified rice starches, physically modified sorghum starches, and physically modified tapioca starches.

* * * * *